United States Patent [19]

Hitzel et al.

[11] 4,325,963

[45] Apr. 20, 1982

[54] THIENOPYRROLONE SUBSTITUTED BENEZENESULFONYLUREAS AND THEIR USE

[75] Inventors: Volker Hitzel, Hofheim am Taunus; Rudi Weyer, Kelkheim; Karl Geisen, Frankfurt am Main; Günter Regitz, Bad Soden am Taunus, all of Fed. Rep. of Germany

[73] Assignee: Hoechst Aktiengesellschaft, Frankfurt am Main, Fed. Rep. of Germany

[21] Appl. No.: 217,526

[22] Filed: Dec. 17, 1980

[30] Foreign Application Priority Data

Dec. 19, 1979 [DE] Fed. Rep. of Germany ....... 2951060

[51] Int. Cl.³ .................... A61K 31/64; C07D 495/04
[52] U.S. Cl. ............................. 424/274; 260/326.23; 260/326.28; 260/326.55 A; 260/454; 549/71
[58] Field of Search .................. 260/326.23; 424/274; 564/40, 41

[56] References Cited

U.S. PATENT DOCUMENTS

| | | | |
|---|---|---|---|
| 3,449,346 | 6/1969 | Aumuller et al. | 564/41 |
| 3,494,936 | 2/1970 | Weyer et al. | 564/40 |
| 3,646,009 | 2/1972 | Winter et al. | 564/40 |
| 3,819,633 | 6/1974 | Ambrogi et al. | 564/40 |
| 3,919,245 | 11/1975 | Weyer et al. | 564/40 |

*Primary Examiner*—Alton D. Rollins
*Attorney, Agent, or Firm*—Curtis, Morris & Safford

[57] ABSTRACT

Sulfonylureas of the formula

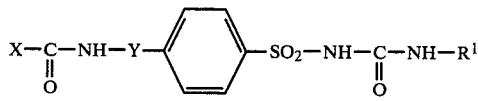

wherein $R^1$, X and Y have the indicated meanings, as well as their physiologically acceptable salts, pharmaceutical preparations on the basis of these compounds and their use in the treatment of diabetes.

9 Claims, No Drawings

THIENOPYRROLONE SUBSTITUTED BENEZENESULFONYLUREAS AND THEIR USE

The invention relates to sulfonylureas of the formula

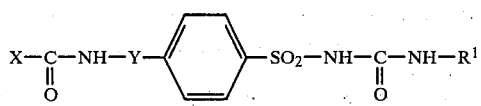

which, as such or in the form of their salts, have blood sugar-lowering properties and are distinguished by a pronounced and long-lasting lowering of the blood sugar level.

In the formula, the symbols have the following meanings:

X is

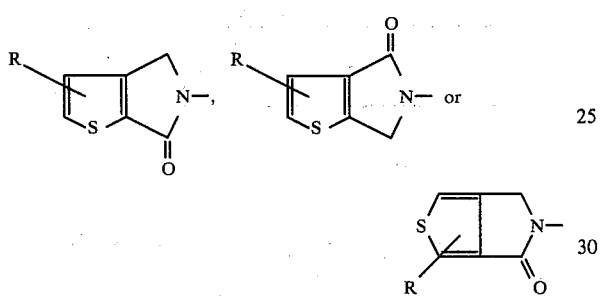

with R being hydrogen or halogen,

Y is alkylene with 2-3 C-atoms, $R^1$ is alkyl with 3 to 8 C-atoms, cycloalkyl, alkylcycloalkyl, dialkylcycloalkyl, cycloalkylalkyl, cycloalkenyl, alkylcycloalkenyl, with from 5-9 C-atoms each, methylcyclopentylmethyl, cyclohexenylmethyl, chlorocyclohexyl, methoxycyclohexyl, bicycloheptyl, bicycloheptenyl, bicycloheptylmethyl, bicycloheptenylmethyl, bicyclooctyl, nortricyclyl, adamantyl or benzyl, X preferably denotes a radical of the formula

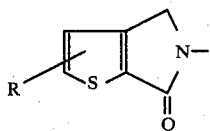

In the formula R preferably denotes hydrogen. Y preferably denotes —CH$_2$—CH$_2$— and

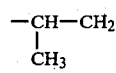

with the —CH$_2$—CH$_2$—group being especially preferred. $R^1$ preferably denotes cyclopentyl, cyclohexyl, methylcyclohexyl, 3-methylcyclopentylmethyl, especially preferred are cyclohexyl and 3-methylcyclopentylmethyl. Bicyclic radicals for $R^1$ are for example: bicyclo[2.2.1]heptyl, bicyclo[2.2.1]heptylmethyl as well as the corresponding unsaturated radicals and the bicyclo[2.2.2]octyl radical.

The invention further relates to processes for the manufacture of these sulfonylureas, pharmaceutical preparations which contain these or consist of these compounds, and their use for the treatment of diabetes.

The processes of manufacture are characterized in that (a) benzenesulfonyl-isocyanates, -carbamic acid esters, -thiolcarbamic acid esters, -ureas, -semicarbazides or -semicarbazones, which are substituted in the 4-position by the group X—CO—NH—Y— are reacted with an amine $R^1$—NH$_2$ or its salts, or sulfonamides of the formula

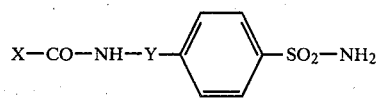

or their salts are reacted with $R^1$-substituted isocyanates, carbamic acid esters, thiolcarbamic acid esters, carbamic acid halides or ureas, (b) benzenesulfonyl-isourea-ethers, -isourea-ethers, parabanic acids or -haloformamidines substituted by the group X—CO—NH—Y— are caused to undergo scission, (c) in X—CO—NH—Y— substituted benzenesulfonylthioureas the sulfur atom is replaced by oxygen, (d) in benzenesulfonylureas of the formula

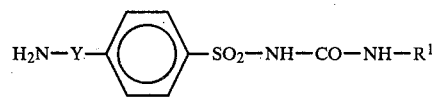

the radical X—CO— is introduced optionally step by step and the reaction products are optionally treated with alkaline agents for formation of salt.

The benzenesulfonyl-carbamic acid esters and -thiolcarbamic acid esters which have been mentioned can contain an alkyl radical or an aryl radical, or even a heterocyclic radical, in the alcohol component. Since this radical is split off during the reaction, its chemical structure has no influence on the character of the end product and can therefore be varied within wide limits. The same is true of the N—$R^1$-substituted carbamic acid esters or the corresponding thiolcarbamic acid esters.

Suitable carbamic acid halides are above all the chlorides.

The benzenesulfonylureas which may be used as starting materials for the process can be unsubstituted, monosubstituted or, in particular, disubstituted on the side of the urea molecule opposite from that carrying the sulfonyl group. Since these substituents are split off during the reaction with amines, their character can be varied within wide limits. In addition to alkyl-, aryl-, acyl- or heterocyclyl-substituted benzenesulfonylureas it is also possible to use benzenesulfonylcarbamoylimidazoles and similar compounds or bisbenzenesulfonylureas which on one of the nitrogen atoms can carry a further substituent, for example methyl. For example, such bis-(benzenesulfonyl)-ureas or N-benzenesulfonyl-N'-acylureas can be treated with $R^1$-substituted amines and the resulting salts can be heated to elevated temperatures, especially to temperatures above 100° C.

Furthermore, it is possible to start from $R^1$-substituted ureas, or from those $R^1$-substituted ureas which are additionally monosubstituted or, in particular, disubstituted at the free nitrogen atom, and to react these with benzenesulfonamides substituted by X—CO—N-H—Y— in the 4-position. Examples of possible starting materials are N-cyclohexyl-urea, the corresponding N'-acetyl-, N'-nitro-, N'-cyclohexyl-, N',N'-diphenyl-, (it being possible for the two phenyl radicals also to be substituted and to be bonded to one another either directly or via a bridge member such as —CH$_2$—, —NH—, —O— or —S—), N'-methyl-N'-phenyl- and N',N'-dicyclohexylureas as well as cyclohexyl-carbamoyl-imidazoles, -pyrazoles or -triazoles, and those of the compounds mentioned which instead of cyclohexyl carry some other substituent falling within the range of definition of R$^1$.

The scission of the benzenesulfonylparabanic acids, -isourea-ethers, -isothiourea-ethers or -haloformamidines mentioned as starting materials is advantageously effected by alkaline hydrolysis. Isourea-ethers can also be very successfully subjected to scission in an acid medium.

The replacement of the sulfur atom in the thiourea grouping of corrspondingly substituted benzenesulfonylthioureas by an oxygen atom can be effected in a known manner, for example with the aid of oxides or salts of heavy metals or by using oxidizing agents, such as hydrogen peroxide, sodium peroxide, nitrous acid or permanganates. The thioureas can also be desulfurized by treatment with phosgene or phosphorous pentachloride. Chloroformamidines or carbodiimides obtained as intermediates can be converted into the benzenesulfonylureas by suitable measures such as hydrolysis or addition reaction with water.

The acylation of the sulfonylureas according to process (d) can be carried out with reactive derivatives of the acid X—COOH such as, for example, halides or urethanes.

The physiologically acceptable salts are manufactured in accordance with methods which are in themselves known. In particular, alkali metal and alkaline earth metal hydroxides, carbonates or bicarbonates, and physiologically tolerated organic bases, are suitable for forming salts.

The synthesis of the oxo-thieno-pyrrole compounds is carried out according to methods known for the manufacture of lactames.

The embodiment of the process according to the invention can in general be varied substantially in respect of the reaction conditions and be suited to the particular circumstances. For example, the reactions can be carried out in the absence or presence of solvents, at room temperature or at an elevated temperature.

Depending on the character of the starting materials, one or other of the processes described can, in some cases, give a desired individual benzenesulfonylurea only in low yields, or can be unsuitable for its synthesis. In such relatively rarely occurring cases it presents no difficulties to an expert to synthesize the desired product by another of the methods described.

The compounds obtained can be purified by dissolution and reprecipitation and/or recrystallization. Alternatively, purification is also possible by liberating the substance from a crystalline (alkali metal) salt by means of a suitable solvent.

The compounds according to the invention are distinguished by valuable pharmacological properties, especially blood sugar-lowering properties. They are therefore suitable for use as medicaments, especially as antidiabetics.

The blood sugar-lowering action of the benzenesulfonylureas described can be ascertained by feeding them as the free compounds, or in the form of the sodium salts in doses of 10 mg or 2 mg/kg to rabbits which have received normal nutrition, and determining the blood sugar value by the known Hagedorn-Jensen method, or by means of an auto-analyzer, over a fairly long period of time.

The determination of the blood sugar-lowering effect can also be carried out with lower doses and according to other known methods.

The following compounds I to VI were administered to rabbits in doses of 2 mg/kg and the blood sugar values were determined by means of an auto-analyzer over a fairly long period of time. The lowering of the blood sugar, thus measured, is shown in the table below in % after 1, 3, 6, 24 and 48 hours.

TABLE

| Compound | Blood sugar-lowering in the rabbit after oral administration of 2 mg/kg in % after | | | | |
|---|---|---|---|---|---|
| | 1 | 3 | 6 | 24 | 48 hours |
| I | 11 | 19 | 33 | 39 | 18 |
| II | 25 | 30 | 38 | 44 | 32 |
| III | 33 | 42 | 37 | 48 | 22 |
| IV | 15 | 36 | 33 | 41 | 11 |
| V | 31 | 32 | 43 | 41 | 42 |
| VI | 20 | 19 | 35 | 35 | 13 |

I N-(4-[2-(6-Oxo-5H-thieno-[2,3-c]-pyrrol-5-yl-carboxamido)-ethyl]-benzenesulfonyl)-N'-(4-methyl-cyclohexyl)-urea
II N-(4-[2-(6-Oxo-5H-thieno-[2,3-c]-pyrrol-5-yl-carboxamido)-ethyl]-benzenesulfonyl)-N'-cyclohexyl)-urea
III N-(4-[2-(6-Oxo-5H-thieno-[2,3-c]-pyrrol-5-yl-carboxamido)-ethyl]-benzenesulfonyl)-N'-(3-methyl-cyclopentylmethyl)-urea
IV N-(4-[2-(6-Oxo-5H-thieno-[2,3-c]-pyrrol-5-yl-carboxamido)-ethyl]-benzenesulfonyl)-N'-$\Delta^3$-cyclohexenyl-urea
V N-(4-[2-(6-Oxo-5H-thieno-[2,3-c]-pyrrol-5-yl-carboxamido)-ethyl]-benzenesulfonyl)-N'-cyclopentylmethyl-urea
VI N-(4-[2-(6-Oxo-5H-thieno-[2,3-c]-pyrrol-5-yl-carboxamido)-ethyl]-benzenesulfonyl)-N'-cycloheptyl-urea.

The acylureido-alkylbenzenesulfonylureas according to the invention are distinguished by a pronounced and longlasting blood sugar-lowering action.

The properties of the compounds make it possible to manage with such low doses in the therapy of diabetes mellitus that the preparation merely re-normalizes the reduced response capacity of the pancreas to an increased blood sugar level.

Benzenesulfonylureas containing a ureidoalkyl radical have already been described on several occasions (DE-PS No. 1,443,911, DE-AS No. 1,670,700, DE-PS No. 1,618,389 and DE-PS No. 2,238,870). It was not to be expected that the compounds according to the invention would be distinguished by the advantageous properties mentioned above.

The sulfonylureas described are preferentially intended for the manufacture of orally administrable preparations for the treatment of diabetes mellitus. They can be administered as such or in the form of their salts or in the presence of materials which lead to salt formation. For example, alkaline agents, such as alkali metal or alkaline earth metal hydroxides, carbonates or bicarbonates may be employed for forming salts. In addition to the sulfonylurea or its salts the preparations can also contain other active compounds.

Suitable medicinal preparations are preferably tablets, which in addition to the sulfonylureas or their salts contain the customary excipients and auxiliaries such as talc, starch, lactose or magnesium stearate.

A preparation which contains the described benzenesulfonylureas as the active compound, for example a tablet or a powder, with or without additives, is advantageously converted to a suitably dosed form. The dose to be selected in this context is such as to suit the activity of the benzenesulfonylurea employed and to suit the desired effect. Advantageously, the dosage per unit is about 0.1 to 10 mg, preferably 0.5 to 2 mg, but dosage units above or below this, which may have to be divided before administration or of which several may have to be taken, can also be used.

The examples which follow show some of the numerous process variants which can be used for the synthesis of the sulfonylureas according to the invention. They are, however, not intended to imply a limitation of the subject of the invention.

The following examples illustrate the invention.

EXAMPLE 1

N-(4-[2-(6-Oxo-5H-thieno-[2,3-c]-pyrrol-5-yl-carboxamido)-ethyl]-benzenesulfonyl)-N'-(4-methyl-cyclohexyl)-urea 3.65 g of 4-(2-[6-oxo-5H-thieno-[2,3-c]-pyrrol-5-yl-carboxamido]-ethyl)-benzenesulfonamide in 100 ml of acetone are stirred after addition of 2.8 g of ground potassium carbonate for 4 hours under reflux. After a short time of cooling, a solution of 1.4 g of 4-methyl-cyclohexyl isocyanate in a small amount of acetone is added dropwise and stirring is continued for another 4 hours under reflux. After cooling, the product is concentrated in vacuo, the residue is taken up in water and the product is acidified with 2 N hydrochloric acid. The precipitate is suctionfiltered, reprecipitated from dilute ammonia solution with 2 N hydrochloric acid and after suction filtering, it is recrystallized from ethanol. The N-(4-[2-(6-Oxo-5H-thieno-[2,3-c]-pyrrol-5-yl-carboxamido)-ethyl]-benzenesulfonyl)-N'-(4-methyl-cyclohexyl)-urea melts at 230°-231° C.

The sulfonamide used as starting material is prepared in the following way:

3-Bromomethyl-thiophene-2-carboxylic acid methyl ester is converted into the hydrochloride of the 3-aminomethylthiophene-2-carboxylic acid methyl ester with a melting point of 202° C. by using the urotropine process. By refluxing the product during 20 hours in methanol/ethanol with addition of potassium carbonate, the 6-oxo-5H-thieno-[2,3-c]-pyrrole with a melting point of 170°-171° C. is obtained. By reaction of the lactam with 2-phenylethyl isocyanate the 6-oxo-5H-thieno-[2,3-c]-pyrrol-2-yl-(N-2-phenylethyl)-carboxamide with a melting point of 124° C. is obtained, from which, by reaction with chlorosulfonic acid and subsequent reaction with concentrated ammonia solution the 4-(2-[6-oxo-5H-thieno-[2,3-c]-pyrrol-5-yl-carboxamido]-ethyl)-benzenesulfonamide with a melting point of 245° C. is obtained.

The following compounds are obtained analogously:

N-(4-[2-(6-Oxo-5H-thieno-[2,3-c]-pyrrol-5-yl-carboxamido)-ethyl]-benzenesulfonyl)-N'-butyl-urea melting point: 180°-181° C. (from ethanol)

N-(4-[2-(6-Oxo-5H-thieno-[2,3-c]-pyrrol-5-yl-carboxamido)-ethyl]-benzenesulfonyl)-N'-propyl-urea melting point: 186°-187° C. (from ethanol)

N-(4-[2-(6-Oxo-5H-thieno-[2,3-c]-pyrrol-5-yl-carboxamido)-ethyl]-benzenesulfonyl)-N'-cyclohexyl-urea melting point: 238°-239° C. (from ethanol-dimethylformamide)

N-(4-[2-(6-Oxo-5H-thieno-[2,3-c]-pyrrol-5-yl-carboxamido)-ethyl]-benzenesulfonyl)-N'-cyclopentyl-urea melting point: 196°-197° C. (from ethanol)

N-(4-[2-(6-Oxo-5H-thieno-[2,3-c]-pyrrol-5-yl-carboxamido)-ethyl]-benzenesulfonyl)-N'-bicyclo-[2.2.1.]-hept-2-yl-methyl-urea melting point: 227°-228° C. (from ethanol-dimethylformamide)

N-(4-[2-(6-Oxo-5H-thieno-[2,3-c]-pyrrol-5-yl-carboxamido)-ethyl]-benzenesulfonyl)-N'-(3-methyl-cyclopentylmethyl)-urea melting point: 196°-197° C. (from ethanol)

N-(4-[2-(6-Oxo-5H-thieno[2,3-c]-pyrrol-5-yl-carboxamido)-ethyl]-benzenesulfonyl)-N'-(3-methyl-cyclopentyl)-urea melting point: 196°-197° C. (from ethanol)

N-(4-[2-(6-Oxo-5H-thieno-[2,3-c]-pyrrol-5-yl-carboxamido)-ethyl]-benzenesulfonyl)-N'-$\Delta^3$-cyclohexenyl-urea melting point: 199°-201° C. (from ethanol)

N-(4-[2-(6-Oxo-5H-thieno-[2,3-c]-pyrrol-5-yl-carboxamido)-ethyl]-benzenesulfonyl)-N'-hexyl-urea melting point: 197°-198° C. (from ethanol)

N-(4-[2-(6-Oxo-5H-thieno-[2,3-c]-pyrrol-5-yl-carboxamido)-ethyl]-benzenesulfonyl)-N'-(4,4-dimethyl-cyclohexyl)-urea melting point: 253°-255° C. (from ethanol)

N-(4-[2-(6-Oxo-5H-thieno-[2,3-c]-pyrrol-5-yl-carboxamido)-ethyl]-benzenesulfonyl)-N'-benzyl-urea melting point: 206°-208° C. (from ethanol)

N-(4-[2-(6-Oxo-5H-thieno[2,3-c]-pyrrol-5-yl-carboxamido)-ethyl]-benzenesulfonyl)-N'-cyclopentylmethyl)-urea melting point: 200°-202° C. (from ethanol)

N-(4-[2-(6-Oxo-5H-thieno-[2,3-c]-pyrrol-5-yl-carboxamido)-ethyl]-benzenesulfonyl)-N'-cycloheptyl-urea melting point: 230°-232° C. (from ethanol)

N-(4-[2-(6-Oxo-5H-thieno-[2,3-c]-pyrrol-5-yl-carboxamido)-ethyl]-benzenesulfonyl)-N'-cyclooctyl-urea melting point: 198°-200° C. (from ethanol)

EXAMPLE 2

N-(4-[2-(6-Oxo-5H-thieno-[2,3-c]-pyrrol-5-yl-carboxamido)-ethyl]-benzenesulfonyl)-N'-cyclohexyl-urea 5.5 g 6-Oxo-5H-thieno-[2,3-c]-pyrrol-2-yl-carboxylic acid chloride (prepared from 6-oxo-5H-thieno-[2,3-c]pyrrolo-Na and phosgene in toluene are introduced into a solution of 11.7 g of N-(4-[2-aminoethyl]-benzenesulfonyl)-N'-cyclohexyl-urea in 100 ml of pyridine. After the addition, the product is heated to 100° C. for 4 hours while stirring, cooled and poured onto ice water. When acidifying cautiously with concentrated hydrochloric acid, a precipitate is formed which is suction filtered, dissolved in dilute ammonia solution, reprecipitated with dilute hydrochloric acid and recrystallized from ethanol-dimethylformamide. The N-(4-[2-(6-Oxo-5H-thieno-[2,3-c]-pyrrol-5-yl-carboxamido)-ethyl]-benzenesulfonyl)-N'-cyclohexyl-urea melts at 236°-238° C. and according to thin layer chromatography it is identical with an authentic sample.

EXAMPLE 3

N-(4-[2-(6-Oxo-5H-thieno-[2,3-c]-pyrrol-5-yl-carboxamido)-ethyl]-benzenesulfonyl)-N'-cyclohexyl-urea 0.75 g of N-(4-[2-(6-Oxo-5H-thieno-[2,3-c]-pyrrol-5-yl-carboxamido)-ethyl]-benzenesulfonyl)-N'-cyclohexylthiourea (melting point: 201°-202° C., prepared from the corresponding sulfonamide with cyclohexyl mustard oil) is heated to 45° C. for 4 hours in 50 ml of methanol and 50 ml of water after addition of 0.32 of g yellow mercury oxide while stirring. After cooling the mercury sulfide is filtered off, the filtrate is concentrated, the remaining residue is suction filtered and recrystallized from ethanol-dimethylformamide. The melting point of the N-(4-[2-(6-Oxo-5H-thieno-[2,3-c]-pyrrol-5-yl-carboxamido)-ethyl]-benzenesulfonyl)-N'-cyclohexyl-urea thus obtained is 235°–237° C. A mixed melting point and a comparison with a sample manufactured in another way by thin layer chromatography, did not shown any difference.

EXAMPLE 4

N-(4-[2-(6-Oxo-5H-thieno-[2,3-c]-pyrrol-5-yl-carboxamido)-ethyl]-benzenesulfonyl)-N'-cyclohexyl-urea 0.75 g of N-(4-[2-(6-Oxo-5H-thieno-[2,3-c]-pyrrol-5-yl-carboxamido)-ethyl]-benzenesulfonyl)-N'-cyclohexylthiourea is stirred in 50 ml of anhydrous methanol after adding 0.32 g of yellow mercury oxide for 6 hours, under reflux. After cooling and filtering, the reaction solution is concentrated and the N-(4-[2-(6-Oxo-5H-thieno-[2,3-c]-pyrrol-5-yl-carboxamido)-ethyl]-benzenesulfonyl)-N'-cyclohexyl-isourea methyl ether with a melting point of 183°–184° C. is obtained.

The isourea methyl ether obtained in the manner described above is heated for 2 hours in 30 ml of concentrated hydrochloric acid on the steam bath. After diluting with water the product is suction filtered and recrystallized from ethanol with addition of dimethylformamide. The N-(4-[2-(6-Oxo-5H-thieno-[2,3-c]-pyrrol-5-yl-carboxamido)-ethyl]-benzenesulfonyl)-N'-cyclohexyl-urea melts at 236°–239° C.

With a sample prepared according to Example 1 the product does not show depression of the mixed melting point and is also identical in the comparison by thin layer chromatography.

EXAMPLE 5

N-(4-[2-(6-Oxo-5H-thieno-[2,3-c]-pyrrol-5-yl-carboxamido)-ethyl]-benzenesulfonyl)-N'-cyclohexyl-urea 1.3 g of N-(4-[2-(6-Oxo-5H-thieno-[2,3-c]-pyrrol-5-yl-carboxamido)-ethyl]-benzenesulfonyl)-carbamic acid methyl-ester (melting point: 214° C., prepared by reaction of 4-(2-[6-Oxo-5H-thieno-[2,3-c]-pyrrol-5-yl-carboxamido]-ethyl-benzensulfonamide with chloroformic acid methyl ester) are dissolved in 50 ml of dioxan. After addition of 0.7 ml of cyclohexylamine the product is heated to 100° C. for 3 hours, while stirring, and the methanol formed is distilled off. After the removal of the solvent the batch is taken up in dilute hydrochloric acid and suction filtered. After reprecipitation from dilute ammonia solution with dilute hydrochloric acid the N-(4-[2-(6-Oxo-5H-thieno-[2,3-c]-pyrrol-5-yl-carboxamido)-ethyl]-benzenesulfonyl)-N'-cyclohexyl-urea is recrystallized from ethanol-dimethylformamide; it melts at 238°–239° C.

The following compound is obtained analogously: N-(4-[2-(6-Oxo-5H-thieno-[2,3-c]-pyrrol-5-yl-carboxamido)-ethyl]-benzenesulfonyl)-N'-(4-chlorocyclohexyl)-urea melting point: 195°–198° C. (from ethanol).

What is claimed is:

1. Sulfonylureas of the formula

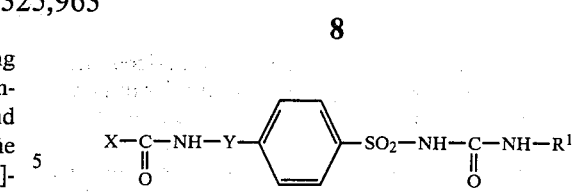

wherein
X is

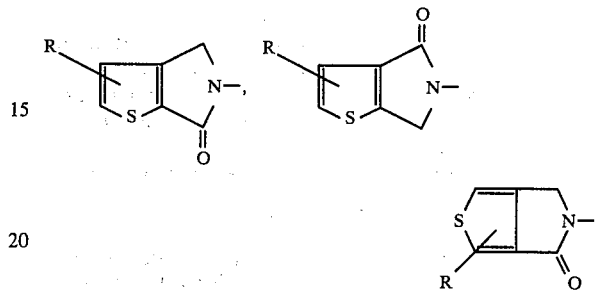

with R being hydrogen or halogen,
Y is alkylene with 2–3 C-atoms,
R is alkyl with 3 to 8 C-atoms, cycloalkyl, alkylcycloalkyl, dialkylcycloalkyl, cycloalkylalkyl, cycloalkenyl, alkylcycloalkenyl, with 5–9 C-atoms each, methylcyclopentylmethyl, cyclohexenylmethyl, chlorocyclohexyl, methoxycyclohexyl, bicycloheptyl, bicycloheptenyl, bicycloheptylmethyl, bicycloheptenylmethyl, bicyclooctyl, nortricyclyl, adamantyl or benzyl and their physiologically tolerated salts.

2. Sulfonylurea of the formula:

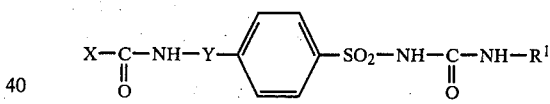

or a physiologically tolerable salt thereof wherein
X is

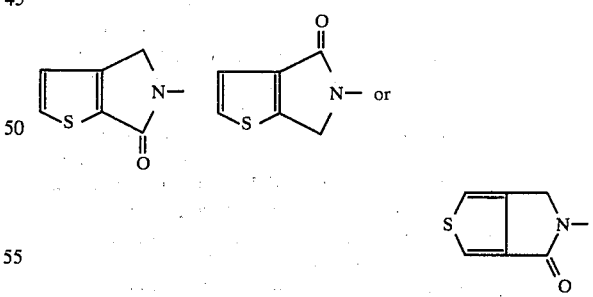

Y is alkylene of 2 to 3 C-atoms, and
R¹ is alkyl of 3 to 8 C-atoms, cycloalkyl, alkylcycloalkyl, dialkylcycloalkyl, cycloalkylalkyl, cycloalkenyl or alkylcycloalkenyl of 5 to 9 C-atoms each, methylcyclopentylmethyl, cyclohexenylmethyl, chlorocyclohexyl, methoxycyclohexyl, bicycloheptyl, bicycloheptenyl, bicycloheptylmethyl, bicycloheptenylmethyl, bicyclooctyl, nortricyclyl, adamantyl or benzyl.

3. Sulfonylurea of the formula:

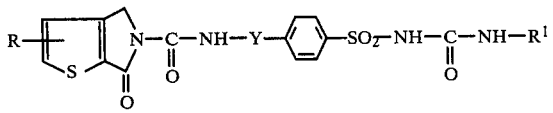

or a physiologically tolerable salt thereof wherein
R is hydrogen or halogen,
Y is alkylene of 2 to 3 C-atoms, and
R$^1$ is alkyl of 3 to 8 C-atoms, cycloalkyl, alkylcycloalkyl, dialkylcycloalkyl, cycloalkylalkyl, cycloalkenyl or alkylcycloalkenyl of 5 to 9 C-atoms each, methylcyclopentylmethyl, cyclohexylmethyl, chlorocyclohexyl, methoxycyclohexyl, bicycloheptyl, bicycloheptenyl, bicycloheptylmethyl, bicycloheptenylmethyl, bicyclooctyl, nortricyclyl, adamantyl or benzyl.

4. Sulfonylurea of the formula

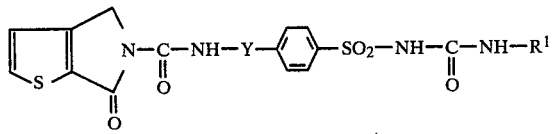

or a physiologically tolerable salt thereof wherein
Y is alkyl of 2 to 3 C-atoms and
R$^1$ is alkyl of 3 to 8 C-atoms, cycloalkyl, alkylcycloalkyl, dialkylcycloalkyl, cycloalkylalkyl, cycloalkenyl or alkylcycloalkenyl of 5 to 9 C-atoms each, methylcyclopentylmethyl, cyclohexylmethyl, chlorocyclohexyl, methoxycyclohexyl, bicycloheptenylmethyl, bicyclooctyl, nortricyclyl, adamantyl or benzyl.

5. The sulfonylurea defined in claim 1 which is N-(4-[2-(6-Oxo-5H-thieno-[2,3-c]-pyrrol-5-yl-carboxamido)-ethyl]-benzenesulfonyl-N'-cyclohexylurea.

6. The sulfonylurea defined in claim 1 which is N-(4-[2-(6-oxo-5H-thieno-[2,3-c]-pyrrol-5-yl-carboxamido)-ethyl]-benzenesulfonyl)-N'-(3-methyl-cyclopentylmethyl)-urea.

7. The sulfonylurea defined in claim 1 which is N-(4-[2-(6-Oxo-5H-thieno-[2,3-c]-pyrrol-5-yl-carboxamido)-ethyl]-benzenesulfonyl)-N'-cyclopentylmethyl-urea.

8. Antidiabetic composition containing, as the essential active ingredient, an effective amount of a compound as defined in claim 1, together with an inert carrier therefor.

9. Process for lowering the blood sugar level in the treatment of diabetes by administering an effective amount of a compound according to claim 1.

* * * * *